United States Patent [19]

Betts

[11] Patent Number: 4,895,025

[45] Date of Patent: Jan. 23, 1990

[54] DESTRUCTIVE INSECT INDUCED VIBRATION DETECTOR

[75] Inventor: William B. Betts, Alva, Okla.

[73] Assignee: Sound Technologies, Inc., Kilgore, Tex.

[21] Appl. No.: 136,843

[22] Filed: Dec. 22, 1987

Related U.S. Application Data

[63] Continuation-in-part of Ser. No. 906,880, Sep. 15, 1986, abandoned.

[51] Int. Cl.⁴ ............................................. G01N 29/00
[52] U.S. Cl. ......................................... 73/587; 73/661
[58] Field of Search ................. 73/584, 587, 391, 632, 73/659, 661; 310/327, 334, 336

[56] References Cited

U.S. PATENT DOCUMENTS 2,875,354  2/1959  Harris .
3,166,730  1/1965  Brown, Jr., et al. .
4,008,711  2/1977  Olinger et al. .
4,629,834  12/1986  Waggoner et al. ................ 381/68.2
4,671,114  6/1987  Litzkow et al. ...................... 73/587
4,701,658  10/1987  Ringermacher et al. ........... 310/327

OTHER PUBLICATIONS

R. C. Barton, "An Audio-Amplifying System for Termite Detection," Termite and Termite Control, 1934, pp. 711-714.
Roy J. Pence, "Electronic Detective Developed by UCLA Uncovers Termites," Pest Control, Nov. 1954, p. 27.
"Electronic Termite Dtection," Physionics Corporation, (publication date unknown).

*Primary Examiner*—John Chapman
*Attorney, Agent, or Firm*—Jerry M. Keys

[57] ABSTRACT

Wood and other article destroying insects, when feeding, induce vibrations in the article being destroyed which is monitored and amplified to an audible level. The vibratory sounds are then analyzed as by comparison with other records of known destructive insects to determine the probable species of insect and its location.

9 Claims, 3 Drawing Sheets

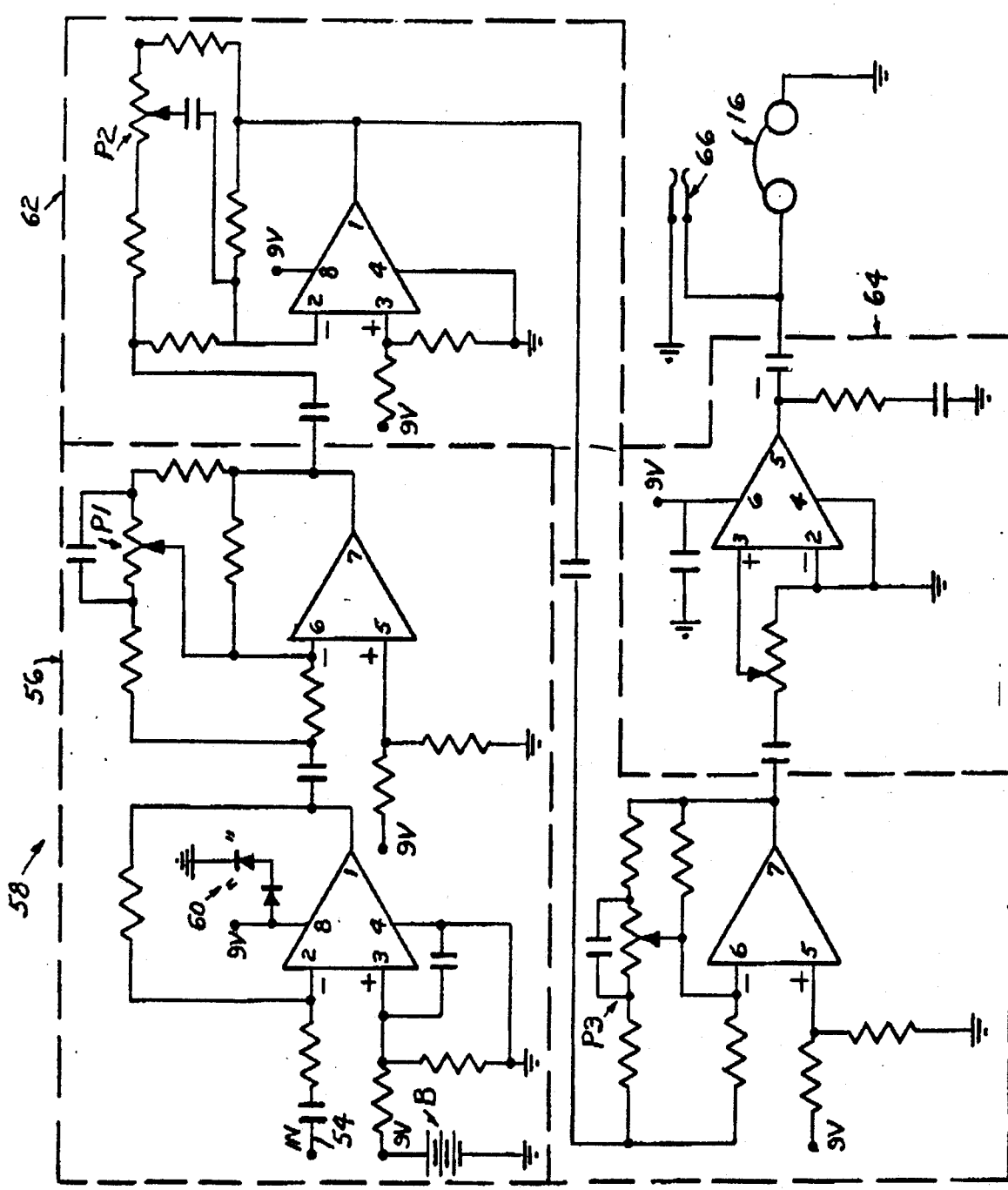
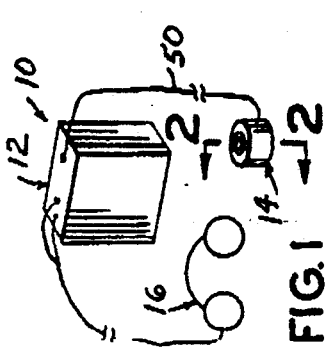
FIG. 1
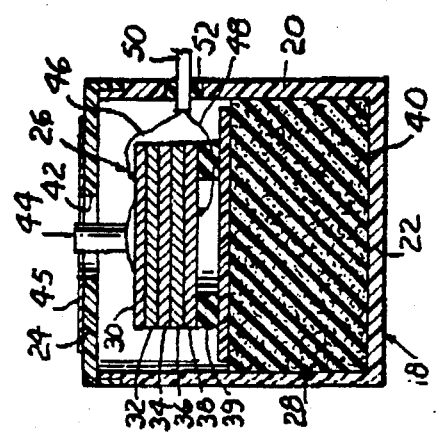
FIG. 2
FIG. 3

DESTRUCTIVE INSECT INDUCED VIBRATION DETECTOR

RELATED APPLICATIONS

This application is a continuation-in-part of my application Ser. No. 906,880 filed Sept. 15, 1986, now abandoned.

BACKGROUND OF THE INVENTION

1. Field of the invention.

The present invention relates to detecting and locating destructive insects and more particularly to an electric circuit for amplifying insect generated vibrations in the articles or objects being destroyed.

As is well known, insect pests have been damaging or destroying food and other articles, such as grain, fruit and wood dwellings or other property for centuries. Such insects are usually invisible, being contained by the articles being destroyed, and must be located and identified in order to provide some means of control and/or elimination. It frequently happens, as in the case of grain destroying insects and termites, extensive damage has been done before insect damage is observed.

This invention provides a portable electrical apparatus which includes a piezoelectric transducer for detecting and amplifying insect or larva produced vibrations and for locating the position or proximity of insects destroying the articles under test.

2. Description of prior art.

Prior patents featuring vibratory sound amplification have generally related to stethoscopes in which a transducer is utilized for monitoring heart beats or the sound of blood produced in passing through heart valves or for detecting fetal heart beats.

Although electronic devices for sensing insect-induced vibrations have been constructed in the past, such devices had only limited practicability due to the need for conflicting design parameters. Such devices needed to be extremely sensitive to pick up the subtle vibrations in a structure or other article caused by insects. Yet if such sensitivity was achieved, the device also picked up a large variety of vibrations caused by other phenomena, as well as human activity. This has typically limited the usefulness of such prior art devices to laboratory-type environments or has required the probe of such devices to actually penetrate the structure or article being tested in order to reduce the noise levels, thereby damaging the structure or article.

In U.S. Pat. No. 4,008,711, an apparatus is disclosed for detecting the probable existence of cerebral aneurysms in which sound waves emanating from the patient's eyes are non-invasively monitored and converted by an electronic microphone into electrical signals which are filtered, amplified, filtered again and recorded on one channel of a magnetic tape. A heart signal, to be utilized as a computer trigger signal, is filtered and recorded on another channel of the tape. The signals are then passed through a final filter to a computer having a Fourier analysis capability. Data recorded over the patient's eyes is sampled by the computer at peak pulse pressure in the cerebral vascular system and the result of the computer analysis is displayed in the form of a spectrum on a cathode ray tube and is plotted to provide a permanent record. The displayed spectrum is considered to indicate the probable existence of an aneurysm if it includes a relatively high energy peak in the range of 200 Hz. to 800 Hz. and having an amplitude one and one-half times greater than the amplitude of any adjacent peak within 50 Hz. frequency of the high energy peak.

This invention is distinctive over such prior art by providing a piezoelectric transducer mechanically connected to a probe containing and capable of noninvasively detecting vibrations in an article being destroyed by insects. The insect destructive actions, such as an insect's bite tearing off a piece of wood cellulose, are amplified sufficiently to permit an operator to hear such vibrations through a headset. Each insect generates its own particular frequency rhythm while it feeds. This frequency pattern, in addition to being heard, may be recorded for later playback and analyzation or computer graph plotted for identifying the insect.

SUMMARY OF THE INVENTION

The invention comprises a small portable unit which may be hand held or strapped to the user's belt and comprises a piezoelectric transducer connected with a filtering and amplifying circuit to provide an audio signal to the headset. The transducer includes a probe manually placed in contact with the object under test, such as a building wall, if testing for termites. The probe is mechanically connected to the piezoelectric material which in turn is connected to a preamplifier. The amplified signal is filtered to a predetermined frequency range and further amplified where it is passed to an audio amplifier operatively coupled to a headset through a volume control.

The principal object of this invention is to provide a vibration detecting apparatus and method for indicating the presence of hidden insects destroying food or an object by which the type of insects and their location may be precisely determined by the audio and/or computer graph printout frequency pattern generated by the insect's destructive actions.

BRIEF DESCRIPTION OF THE DRAWINGS

FIG. 1 is a perspective view of the apparatus;

FIG. 2 is a vertical cross sectional view of the transducer portion of the apparatus, to enlarged scale, taken along the line 2—2;

FIG. 3 is a wiring diagram;

DESCRIPTION OF THE PREFERRED EMBODIMENTS

Figure 4:
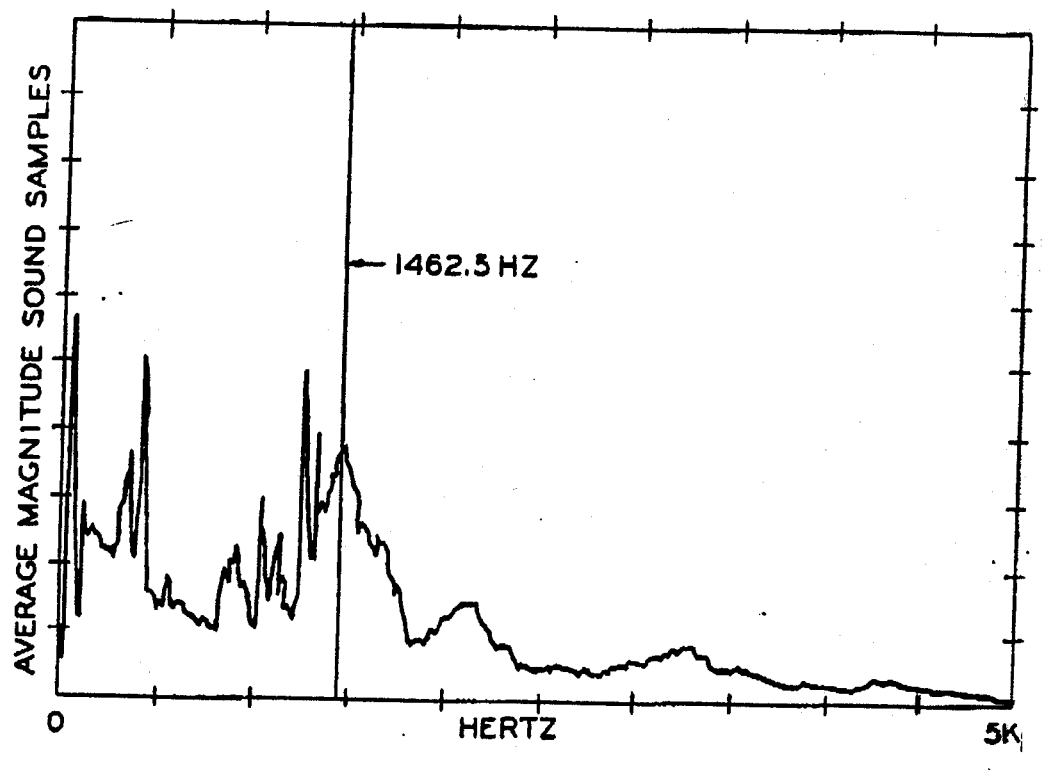
FIGS. 4 and 5 are graphs illustrating the vibratory patterns produced by wood-destroying insects.

Like characters of reference designate like parts in those figures of the drawings in which they occur.

In the drawings:

The reference numeral 10 indicates the apparatus comprising a circuit containing housing 12, a transducer 14 and earphones or headset 16 connected with the housing contained circuit.

Referring more particularly to FIG. 2, the first embodiment the transducer 14 comprises a cylindrical dielectric case or housing 18 having an annular wall 20 and closed ends 22 and 24 and loosely surrounding a piezoelectric assembly 26 and its mounting assembly 28.

The piezoelectric assembly 26 is generally circular of a smaller diameter than the inside diameter of the case 18 and comprises a plurality, preferably five, layers in superposition. The top layer 30, as viewed in the drawing, is silver, the next or underlying layer being piezolectric material 32, the next or middle layer being copper 34 and overlying another layer of piezolectric material 36 which overlies the final or bottom layer of silver 38. The layers of the piezoelectric material 32 and 36 may be formed from either natural or manmade crystals or ceramic materials, or a combination thereof.

The crystal assembly 26 also may be a rectangular bar or a square, as well as a circular device so long as the stress placed on the piezoelectric material causing the strain on the piezoelectric material to operate in the direction needed to cause piezoelectric activity. A round or square shape is preferred because it has been found that such shapes will not break as easily under stress as a bar-shaped piezoelectric assembly.

The piezoelectric assembly 26 is axially supported, as a unit, in the transducer case 18 by mounting assembly 28, which preferably comprises a nonconductive mounting platform 39 and a section of foam rubber 40 filling the bottom half of the case and secured to the inner surface of the case wall 20 and bottom end 22. The mounting platform 39, preferably a rubber ring, is interposed between the piezoelectric assembly 26 and foam rubber 40 and bonded to the silver layer 38 of the piezoelectric assembly and adjacent end surface of the foam 40. This disposes the other or top silver layer 30 adjacent but spaced from the case end 24. The case end 24 is centrally apertured, as to 42, for loosely surrounding a relatively short small diameter cylindrical probe 44, having one end centrally secured axially to the top silver layer 30 of assembly 26. The other or free end of the probe 44 projects beyond the plane of the case end wall 24 and a relatively thin flat washer 45, concentric with the case opening 42, a relatively short distance, for example, 1/16 inch for the purposes presently explained.

The probe 44 is preferably of a hard material, such as a hard plastic, which has its free end formed to be placed in close contact with the structure or article under test. Since stress will be applied through the probe to the piezoelectric assembly 26 when the probe 44 is placed in contact with an article, the foam rubber 40 cushions the impact of any stress transmitted through the probe 44 to the piezoelectric assembly 26, thereby essentially allowing the piezoelectric assembly and probe to "float" within the case 18. It should be noted, however, that other resilient material that allows the piezoelectric assembly 26 to essentially float within the case may also be substituted for the foam rubber 40.

Two wires 46 and 48 are respectively connected at one end with the end most silver layers 30 and 38 of the piezoelectric assembly 26. The other ends of these two wires are connected with a shielded cable 50 extending through a grommet 52 in the transducer case wall and connected with the input 52 of the preamp circuit 56 forming a part of the circuit 58 (FIG. 3).

Figure 6:
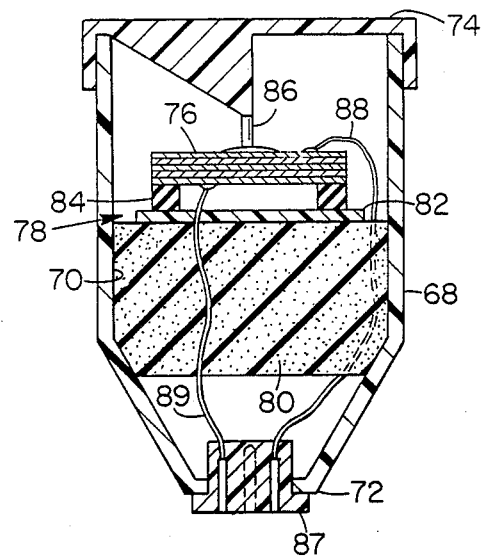
FIG. 6 is a vertical cross sectional view of a second embodiment of the transducer of the apparatus.

In a second embodiment of the transducer 14 of the present invention (FIG. 6), a dielectric or non-conductive housing or case 68 having an annular wall 70 and a closed end 72 loosely surrounds a piezoelectric assembly 76 and its mounting assembly 78. The case 68 also has an open top end across which a specially designed diaphragm 74 may be mounted.

The piezoelectric assembly 76 may be in the form of a rectangular prism, a square, or a circle. Preferably, the geometric design of the piezoelectric crystal is circular or square for the reasons set forth above relative to the first embodiment. The piezoelectric assembly 76 may otherwise be constructed in a similar manner to the piezoelectric assembly 26 discussed earlier.

The piezoelectric assembly 76 is supported as a unit in transducer housing 68 by a mounting assembly 78, which preferably comprises a section of resilient material 80, such as foam rubber, which fills the case bottom half and which is secured to the inner surface of the case wall 70 and bottom end 72 by suitable means. A mounting platform 82 is attached to the upper surface of the resilient material 80 for supporting the piezoelectric assembly 76.

A plurality of mounting members 84, preferably rubber rings, are interposed between the piezoelectric assembly 76 and mounting platform 82 of the mounting assembly and bonded to the bottom silver layer of the piezoelectric assembly 76 and the upper surface of the mounting platform 82.

This disposes the top silver layer of the piezoelectric assembly 76 adjacent but spaced from an open top end of the transducer case 68 upon which a specially designed diaphragm 74 is fastened to the case by suitable means.

The diaphragm 74 is constructed of hard but flexible plastic material rather than the materials historically used to construct diaphragms for stethoscopes in order to increase the sensitivity of diaphragm 74 to the higher frequencies normally associated with insect vibrations, rather than the low frequencies associated with human heart beats. Preferably diaphragm 74 is constructed so that its thickness is nonuniform. The diaphragm 74 includes a force directing member or internal probe 86 for concentrating the stress or force induced into the diaphragm 74 by vibrations in the structure and directing such forces to one point on the piezoelectric assembly 76. Alternatively, the internal probe 86 may be constructed separately and attached to the diaphragm 74. The internal probe 86 is also attached to the piezoelectric assembly 76 by suitable means as discussed in more detail below.

The second embodiment of the transducer 14 has significant advantages in that it provides substantially similar sensing capabilities to the external probe of the first embodiment without having the disadvantages of an external probe which may break off when not used in a careful manner.

Due to the subtle nature of the insect vibrations sought to be detected, the piezoelectric assemblies 26 and 76 should be mounted to generate significant strain in the piezoelectric materials for only small variations in the stress applied through the probes to the piezoelectric materials. It has been found that sensitivity to such minor stress forces may be enhanced by mounting the piezoelectric assemblies 26 or 76 to their respective mounting assemblies so that the piezoelectric assembly becomes unbalanced when stress is applied through the probe to an off center point on the assembly and the internal end of the external probe 44 in the first embodiment, or the internal probe 86 of the second embodiment, is attached to the top layer 30 of the piezoelectric assembly at a point which creates shear, as well as compressive forces, on the piezoelectric material.

Figure 7A:
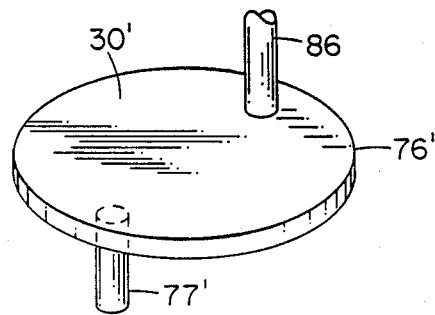
FIG. 7A is a perspective view of a circular piezoelectric crystal and a configuration for mounting it.

With respect to a circular-shaped piezoelectric assembly (FIG. 7A), the circular assembly 76 may be mounted to the respective mounting assembly at one or more points 77 and the internal end of the probe 86 is attached to the piezoelectric assembly by suitable means to a point off center of the mounting point 77, if one, or off center from any line segment between any plurality of mounting points. The stress forces applied through a probe to the off center point of the assembly will generate more strain in the piezoelectric material due to the unbalanced application of the stress forces through the probe.

Figure 7B:
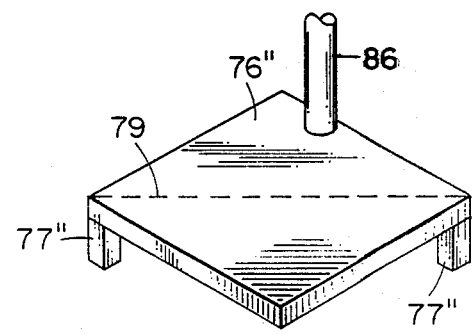
FIG. 7B is a perspective view of a square piezoelectric crystal and a configuration for mounting it.

With respect to a square piezoelectric assembly (FIG. 7B), the square assembly 76 is mounted to the mounting assembly at only two non-adjacent corners points 77 and the internal end of the probe 86 is attached to the square piezoelectric assembly at a point off the diagonal line 79 between the two points at which the square assembly piezoelectric is attached to the mounting assembly.

Two wires 88 and 89 are respectively connected at one end with the endmost silver layers 30 and 38 of the piezoelectric assembly 76. The other ends of these two wires are connected to output connector 87 adapted into the case wall by conventional means and connected with the input 52 of the preamp circuit 56 forming a part of the circuit 58 (FIG. 3).

The preamp circuit 56 of the circuit 58 is formed by an IC chip No. LM 1458 forming a high pass filter which passes frequencies above approximately 350 Hertz.

The circuit 58 is energized by a 9 volt dry cell battery B connected with the positive input pin 3 of the IC1A amplifier and similar pins of the other amplifier components where indicated.

The preamp circuit 56 is operated with an open feedback for peak amplification and includes a LED diode 60, to indicate en the circuit is energized and a first potentiometer P1 for the purposes presently explained.

The signal from the preamp circuit 56 is passed to a low pass filter circuit 62 similarly formed by an IC chip LM 1458 and includes two potentiometers P2 and P3. This filter 62 eliminates all frequencies above 3,500 Hertz, for example, for the reason insect generated frequency vibrations are below this value.

The potentiometer settings are adjusted by using an oscilloscope, not shown, in a known manner.

The frequencies under 3500 Hertz are passed to an audio amplifier 64 formed by an IC chip LM 386 which further amplifies the signal from the transducer 14 to produce a desired audio, controlled by the settings of the potentiometers P1, P2 and P3, at the headset 16. The headset 16 is preferably padded to eliminate extraneous sounds and reduce feedback. A jack 66, connected with the audio output passes the audio signal to a tape recorded and/or microcomputer, not shown, when desired.

Figure 5:
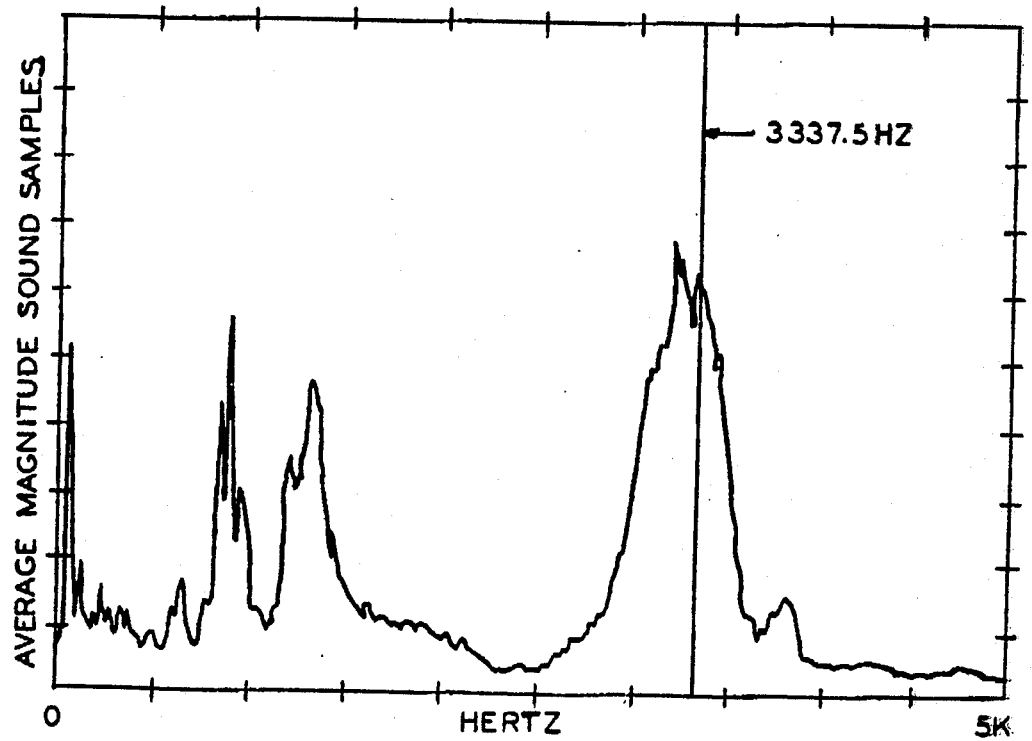

Referring to FIGS. 4 and 5, FIG. 4 graph depicts the wave or frequency pattern of active carpenter ants in which the amplitude of the average of sound vibrations induced by the destructive action of the carpenter is shown by the Y axis of the graph. The vertical line across the graph at 1462.5 Hz is the end of cut-off point and is the limit of the frequency of the actions of this insect in destroying wood.

Similarly, the graph of FIG. 5, representing the average magnitude of sound vibration of a plurality of active termites destroying wood, is shown on the Y axis of the graph with the vertical line or upper limit of the insect induced vibrations at 3337.5 Hz on the X axis of the graph.

Each insect produces its own frequency rhythm while it feeds. This pattern can be heard through the headset or recorded to be played back later and analyzed through a fast Fourier transform, spectrum analyzer, and oscilloscope and then processed through a computer or plotted on a graph.

With the printout of such graphs it seems obvious that an operator can compare them with a known pattern, detect the difference between and identify a particular insect. In the absence of graphs, with a little practice an operator, by listening to magnetic tape records of known insects, soon learns to distinguish between the vibrations produced in an object containing insects being monitored and with considerable accuracy is able to identify the type of insect.

Operation

In operation, the operator places the headset over his ears and manually carries the housing 12 and with one hand manually places the probe end of the transducer 14 in contact with the surface of the area suspected of containing insects. Obviously, all extraneous or surrounding noises are, if possible, substantially eliminated prior to and during such tests. When, for example testing the walls of a building for termites, the probe must be successively placed in contact with the several walls of the building.

Obviously the invention is susceptible to changes or alterations without defeating its practicability. Therefore, I do not wish to be confined to the preferred embodiment shown in the drawings and described herein.

I claim:

1. An apparatus for non-invasively detecting the presence of hidden insects actively destroying an article comprising:
    (a) transducer means for directly detecting the vibrations in the article and generating electrical signals in response to the detected vibrations, wherein said transducer means includes:
        (i) a housing having an aperture formed therein;
        (ii) piezoelectric means situated inside said housing which generates electrical signals in response to mechanical stresses applied thereto;
        (iii) probe means extending through the aperture in said housing wherein said probe means has a free end situated outside said housing for placement in contact with the article to be inspected and a fixed end situated inside said housing which is attached to said piezoelectric means for directing the vibrations from the article through said probe means to said piezoelectric means; and
        (iv) mounting means for flexibly mounting said piezoelectric means inside said housing wherein said piezoelectric means is mounted on the mounting means such that piezoelectric means becomes unbalanced when stress is applied to said piezoelectric means by vibrations transmitted through said probe means;
    (b) means for selectively amplifying the portion of the electrical signals representative of the frequency range of vibrations generated by insects which may inhabit such articles; and
    (c) means for analyzing the electrical signals representative of the vibrations to identify the species within the article.

2. The apparatus of claim 1, wherein:

(a) said piezoelectric means is substantially square and is attached to said mounting means at non-adjacent corners of said square piezoelectric means; and (b) said probe means is attached to said piezoelectric means at a point off the line between the non-adjacent corners of said square piezoelectric means.

3. The apparatus of claim 1, wherein:

(a) said piezoelectric means is substantially circular in design and is mounted to said mounting means by at least one point such that it is unbalanced when pressure is applied at any other point on said piezoelectric means, (b) said probe means is attached to said piezoelectric means at a point other than the point where said piezoelectric means is mounted to said mounting means.

4. The apparatus of claim 1, wherein the mounting means comprises:
resilient material.

5. An apparatus for non-invasively detecting the presence of hidden insects actively destroying an article, comprising:

(a) piezoelectric transducer means for directly detecting the vibrations in the article and generating electrical signals in response to the detected vibrations; wherein said transducer means includes:

(1) a housing having an opening formed in one end thereof;

(2) piezoelectric means situated inside said housing which generates electrical signals in response to mechanical forces applied thereto;

(3) mounting means for flexibly mounting said piezoelectric means inside said housing; and (4) diaphragm means mounted over the opening of said housing for detecting vibration forces in an article and transferring such forces to said piezoelectric means when said diaphragm means is placed in contact with the article, wherein said diaphragm means includes (1) a flexible portion of nonuniform thickness which vibrates in response to the vibration forces in the article;

(2) an internal force directing portion attached to said piezoelectric means for concentrating and directing the vibration forces applied to said flexible portion of said diaphragm means to said piezoelectric means;

(b) means for selectively amplifying the portion of the electrical signals representative of the frequency range of vibrations generated by insects which may inhabit such articles; and (c) means for analyzing the electrical signals representative of the vibrations to identify the species within the article.

6. The apparatus of claim 5, wherein: said sensing portion of the diaphragm means is made from hard flexible material responsive to vibrations typically associated with insects.

7. The apparatus of claim 6, wherein: said piezoelectric means is mounted on said mounting means such that said piezoelectric means becomes unbalanced when stress is applied to said piezoelectric means by vibrations transmitted through said diaphragm means.

8. The apparatus of claim 7, wherein:

(a) said piezoelectric means is substantially square and is attached to said mounting means at nonadjacent corners of said square piezoelectric means; and (b) said internal force directing portion of said diaphragm means is attached to said piezoelectric means at a point off the line between the nonadjacent corners of said square piezoelectric means.

9. The apparatus of claim 7, wherein:

(a) said piezoelectric means is substantially circular in design and is mounted to said mounting means by at least one point such that it is unbalanced when pressure is applied at any other point on said piezoelectric means; and (b) said internal force directing portion is attached to said piezoelectric means at a point other than the point where said piezoelectric means is mounted to said mounting means.

* * * * *